US009551655B2

United States Patent
Mazumder et al.

(10) Patent No.: US 9,551,655 B2
(45) Date of Patent: Jan. 24, 2017

(54) METAMATERIAL SENSOR PLATFORMS FOR TERAHERTZ DNA SENSING

(71) Applicant: The Regents of The University of Michigan, Ann Arbor, MI (US)

(72) Inventors: Pinaki Mazumder, Ann Arbor, MI (US); Nan Zheng, Ann Arbor, MI (US); Kyungjun Song, Ann Arbor, MI (US); Mahdi Aghadjani, Ann Arbor, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 5 days.

(21) Appl. No.: 14/810,540

(22) Filed: Jul. 28, 2015

(65) Prior Publication Data

US 2016/0025625 A1    Jan. 28, 2016

Related U.S. Application Data

(60) Provisional application No. 62/029,770, filed on Jul. 28, 2014.

(51) Int. Cl.
*G01J 5/00*    (2006.01)
*G01N 21/3581*    (2014.01)
(Continued)

(52) U.S. Cl.
CPC ...... *G01N 21/3581* (2013.01); *G01N 21/0303* (2013.01); *G01N 21/253* (2013.01)

(58) Field of Classification Search
CPC ............ G01N 21/3581; G01N 29/2418; G01N 29/036; G01N 2291/02466
(Continued)

(56) References Cited

U.S. PATENT DOCUMENTS 7,826,504 B2    11/2010 Chen et al.
8,097,854 B2    1/2012 Nagel
(Continued)

FOREIGN PATENT DOCUMENTS

WO    WO-2008109706 A1    9/2008

OTHER PUBLICATIONS

Nagel et al."A functionalized THz sensor for marker-free DNA analysis", Phys. Med. Biol. vol. 48, pp. 3625-3636, 2003.*
(Continued)

*Primary Examiner* — David Porta
*Assistant Examiner* — Meenakshi Sahu
(74) *Attorney, Agent, or Firm* — Harness, Dickey & Pierce, PLC

(57) ABSTRACT

A sensor platform is provided for interrogating a sample with an electromagnetic (EM) wave. The platform includes: a dielectric material having opposing first and second planar surfaces; a first array of loop elements embedded in the first planar surface of the dielectric material, wherein slots are formed between the loop elements in the first array of loop elements and configured to host a sample material therein; and a second array of loop elements embedded in the second planar surface of the dielectric material and formed symmetrically with respect to the first array of loop elements, wherein slots are also formed between the loop elements of the second array of loop elements. The loop elements in the first array and the second array are comprised of a conductive material.

15 Claims, 12 Drawing Sheets

(51) Int. Cl.
*G01N 21/03* (2006.01)
*G01N 21/25* (2006.01)

(58) Field of Classification Search
USPC ..................................................... 250/338.1
See application file for complete search history.

(56) References Cited

U.S. PATENT DOCUMENTS 8,309,925 B2   11/2012   Mendis et al.
2015/0338341 A1*  11/2015  Bifone ................. G01N 29/036
                                                    250/338.1

OTHER PUBLICATIONS

K. Song et al's "Design of Highly Selective Metamaterials for Sensing Platforms", 15340-437X, IEEE (2013).
Neshat, et al's "A THz Transducer for On-Chip Label-Free DNA Sensing", Optical Society of America, (2007).
B. Li, et al's "A Symmetrical Dual-Band Terahertz Metamaterial With Cruciform and Square Loops", Progress in Electromagnetics Research C, vol. 33, pp. 259-267, (2012).
Zheng, et al's "Metamaterial Sensor Platforms for Terahertz DNA Sensing", Proceedings of the 13th IEEE International Conference on Nanotechnology, Beijing, China (2013).

* cited by examiner

METAMATERIAL SENSOR PLATFORMS FOR TERAHERTZ DNA SENSING

CROSS-REFERENCE TO RELATED APPLICATIONS

This application claims the benefit of U.S. Provisional Application No. 62/029,770, filed on Jul. 28, 2014. The entire disclosure of the above application is incorporated herein by reference.

GOVERNMENT INTEREST

This invention was made with government support under EECS1059177 awarded by the National Science Foundation. The Government has certain rights in the invention.

FIELD

The present disclosure relates to a metamaterial sensor platform for Terahertz biosensing.

BACKGROUND

Terahertz sensing has attracted numerous research activities in past decades. Due to the fact that many materials exhibit unique spectrum signatures in THz, different materials can be easily characterized in this band. Although a lot of research are focused on wideband sensing that are trying to capture fingerprint of different materials in THz, narrow band THz bio-sensing based on resonance has been pursued extensively as well since binding state of DNA can be identified through its refractive index change in THz. Traditionally, the change in DNA state from the single-stranded DNA to the double-stranded DNA molecules is investigated by tagging the target DNA with certain agents such as fluorescent ones. Although this method has widespread applications in DNA sensing, it has disadvantages such as the unwanted interference from the tagging agent and the extra preparatory steps. For biomolecule like DNA, its refractive index depends on its binding state to known probes. Therefore measurement of the change in refractive index enables the label-free direct detection and identification of genetic sequences. In M. Gagel, et al's "Integrated THz technology for label-free genetic diagnostics," Applied Physics Letters, Vol. 80, No. 1, pp 154-156, (2002) and P. Bolivar, et al's "Label-free THz sensing of genetic sequences: Towards THz biochips'," Philos. Tran. R. Soc. London Ser. A Math, Phys. Eng. Sci., Vol. 362, pp. 323-333 (2004), integrated on-chip microstrip line resonator is employed to sense refractive index change in DNA. A split ring resonator (SRR) on a paper substrate is demonstrated to have capability to distinguish glucose solutions with different concentrations.

Generally speaking, there are two important aspects in THz DNA resonance sensing. One is to increase sensitivity of the sensor. Various high Q resonators, such as asymmetric split ring resonators (ASRs), Ω-shaped resonator, are developed to achieve this. Another aspect is to reduce the amount of sample needed to characterize it. For example a near field source is employed in W. Withayachumnankul et al's "Sub-diffraction thin-film sensing with planar terahertz metamaterials", Optics Express, Vol. 20, No 9. 3, pp 3345-3352 (2012) to focus the energy onto a tiny spot beyond the diffraction limit, which consequently reduces the amount of sample needed.

In this disclosure, subwavelength scatterers are combined together to produce high order response that is useful to increase sensitivity of the DNA sensors. Three different sensing structures are proposed. Analysis is made based on their circuit models. Full-wave simulation results are also included to demonstrate performance of these sensors.

This section provides background information related to the present disclosure which is not necessarily prior art.

SUMMARY

This section provides a general summary of the disclosure, and is not a comprehensive disclosure of its full scope or all of its features.

A sensor platform is provided for interrogating a sample with an electromagnetic (EM) wave. The platform includes: a dielectric material having opposing first and second planar surfaces; a first array of loop elements embedded in the first planar surface of the dielectric material, wherein slots are formed between the loop elements in the first array of loop elements and configured to host a sample material therein; and a second array of loop elements embedded in the second planar surface of the dielectric material and formed symmetrically with respect to the first array of loop elements, wherein slots are also formed between the loop elements of the second array of loop elements. The loop elements in the first array and the second array are comprised of a conductive material.

In one aspect, the loop elements in the first array and the second array are dimensioned smaller than the given operating wavelength and, in particular, are dimensioned for an electromagnetic (EM) wave having a frequency on the order of one terahertz.

Further areas of applicability will become apparent from the description provided herein. The description and specific examples in this summary are intended for purposes of illustration only and are not intended to limit the scope of the present disclosure.

DRAWINGS

Figure 1:
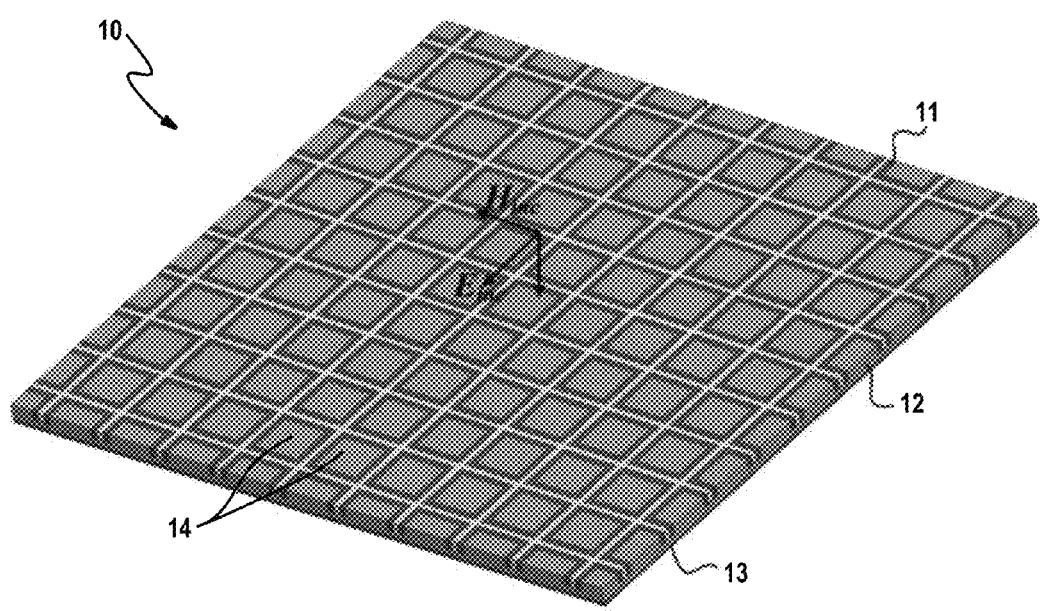
FIG. 1 is a diagram of an example metamaterial sensor platform.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Example embodiments will now be described more fully with reference to the accompanying drawings.

Configuration of an example bio-sensing platform 10 in this disclosure is illustrated in FIG. 1. A metamaterial sensor platform 10 shown in the figure consists of three layers: an upper reactance layer 11, dielectric coupling layer 12 and a lower reactance layer 13. Two reactance layers 11, 13 are composed by periodic subwavelength scatterers 14 that are operating in metamaterial regime (i.e., its size is much smaller than the operating wavelength). Different from the traditional frequency selective surface (FSS) whose selectivity is based on capacitance and inductance provided by high order Floquet mode, this metamaterial sensor relies on the resonance characteristics of small scatters. Some traditional FSSs can indeed have a very sharp pass-band or stop-band. Especially when the FSS operating near the Wood-Rayleigh anomaly, the extraordinary transmission, however, is mainly determined by the period of the scatters instead of their individual feature. Therefore, metamaterial sensors based on resonant subwavelength scatterers will be more sensitive to the sample around it that can change its resonance feature.

When a sensing test is performed, a plane wave is incident normally onto the sensing platform 10, and a receiver is located at the other side to detect the transmission signal. Depending on types of small scatterers, a transmission peak, dip or both of them can occur. By putting samples with different refractive indices on the right location of the sensor, change in these transmission characteristics can be observed, which can help to distinguish different samples. While specific reference is made to electromagnetic waves having a frequency on the order to one terahertz, it is understood that the sensor platform 10 is applicable to signals having different frequencies, for example ranging from 100 GHz to 30 THz.

With such a periodic structure, electromagnetic response of a unit cell is enough to determine response of the entire sensor. In the following section, physical circuit model and numerical HFSS full-wave simulation are combined to analyze different sensor structure and provide a guide to design them. In the full-wave simulation, all metals and dielectrics are assumed to be perfect electric conductor and ideal dielectric without loss, respectively. Periodic boundary conditions are forced at four sides around the unit cell. Plane wave is illuminated from one of those two sides that are parallel with the sensor platform as shown in FIG. 1, and transmitted wave is detected from the other side.

Figure 2A:
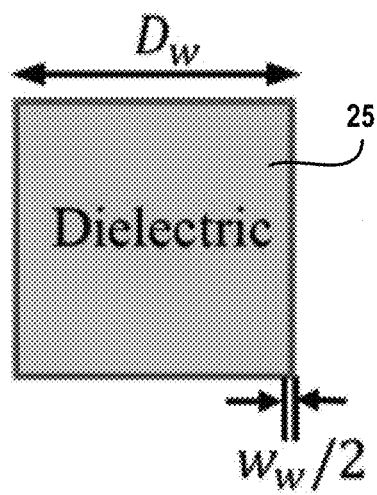
FIGS. 2A and 2B are top views of a dielectric coupling layer and an upper reactance layer, respectively, for a first embodiment of a unit cell of the metamaterial sensor platform.
Figure 2B:
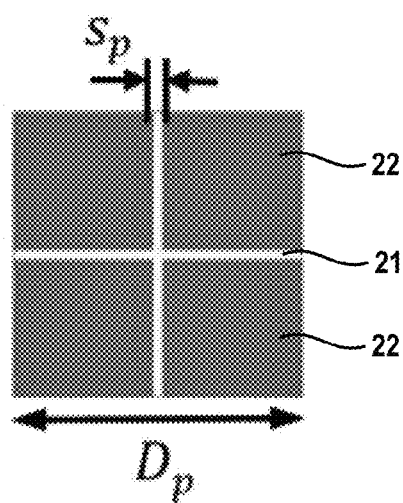
Figure 2C:
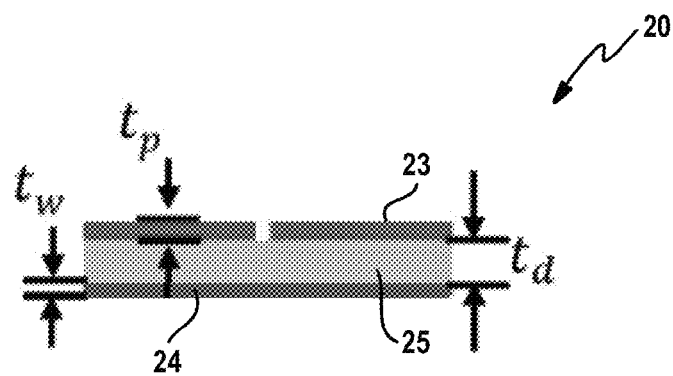
FIG. 2C is a cross-sectional view of the first embodiment of the unit cell of the metamaterial sensor platform.
Figure 3A:
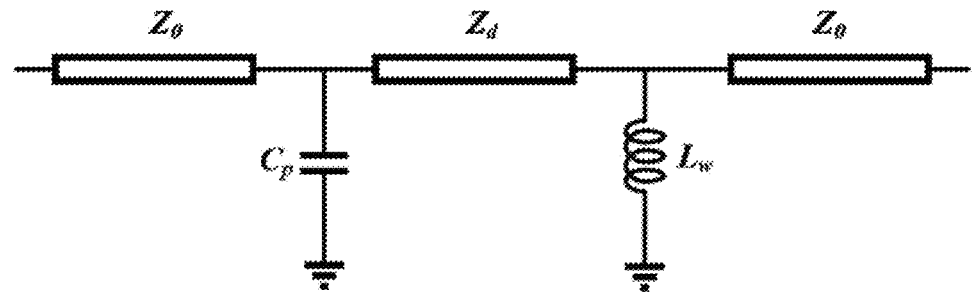
FIGS. 3A-3C are circuit models for a unit cell of the first embodiment of the metamaterial sensor platform with the dielectric coupling layer modeled as a short transmission line, with the dielectric coupling layer modeled as a network and with shunt capacitors neglected, respectively.

The first example embodiment is a patch-wire structure 20 shown in FIGS. 2A-2C whose equivalent circuit is shown in FIG. 3A. In this arrangement, a dielectric coupling layer 25 is sandwiched between a patch layer 23 and a wire layer 24. The patch layer 23 is partitioned by a series of slots 21, thereby forming an array of different patches 22. The patch layer 23 and the wire layer are comprised of a metal (e.g., silver, gold, or copper) or another type of conductive material. In the example embodiment, the coupling layer 25 is comprised of a dielectric material 25 such as SU-8 or Parylene although other types of dielectric materials are contemplated by this disclosure.

Charge deposition along the slots 21 between different patches 22 provides the capacitance $C_p$, while current flow through wire layer 24 contributes to the inductance $L_w$. An approximate equation to estimate $C_p$ and $L_w$ are shown in (1) and (2).

$$C_p = \varepsilon_0 \varepsilon_{\mathit{eff}} \frac{2D_p}{\pi} \ln\left[\left(\sin\frac{\pi S_p}{2D_p}\right)^{-1}\right] \quad (1)$$

$$L_w = \mu_0 \mu_{\mathit{eff}} \frac{D_w}{2\pi} \ln\left[\left(\sin\frac{\pi w_w}{2D_w}\right)^{-1}\right] \quad (2)$$

$Z_0$ and $Z_d$ are wave impedance in free space and dielectric, respectively. This equivalent circuit is valid when the patch layer 23 and wire layer 24 are infinitesimally thin. When thickness of these two layers are moderate, two series reactances are needed to represent influence of the thickness. However, their existence will not, at least qualitatively, influence this analysis much. Thus for the sake of simplicity, they are omitted in the equivalent circuit.

Figure 3B:
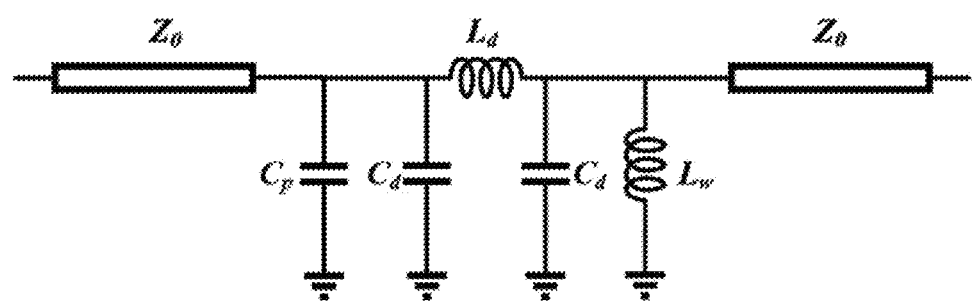
Figure 3C:
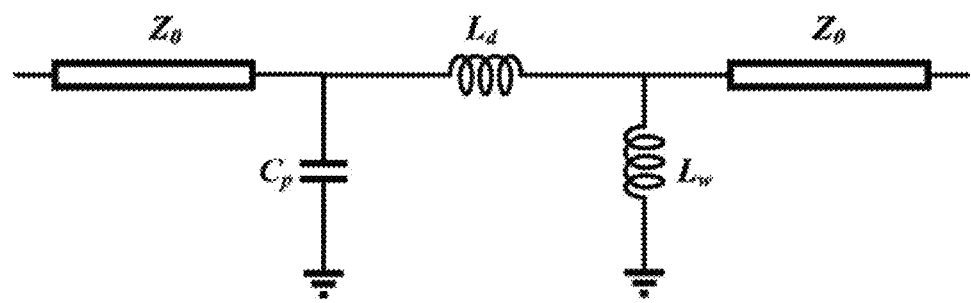
Figure 4A:
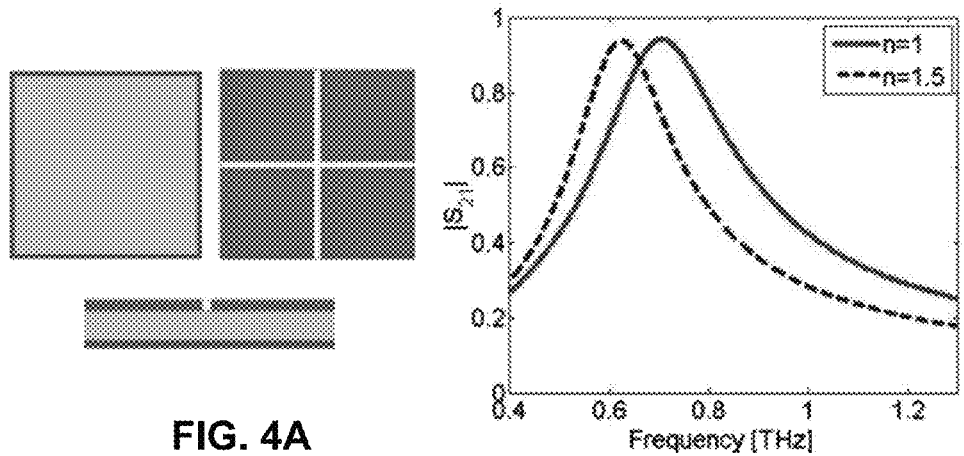
FIGS. 4A-4C are graphs depicting full-wave simulation results for the first embodiment of the metamaterial sensor platform and variants thereof.
Figure 4B:
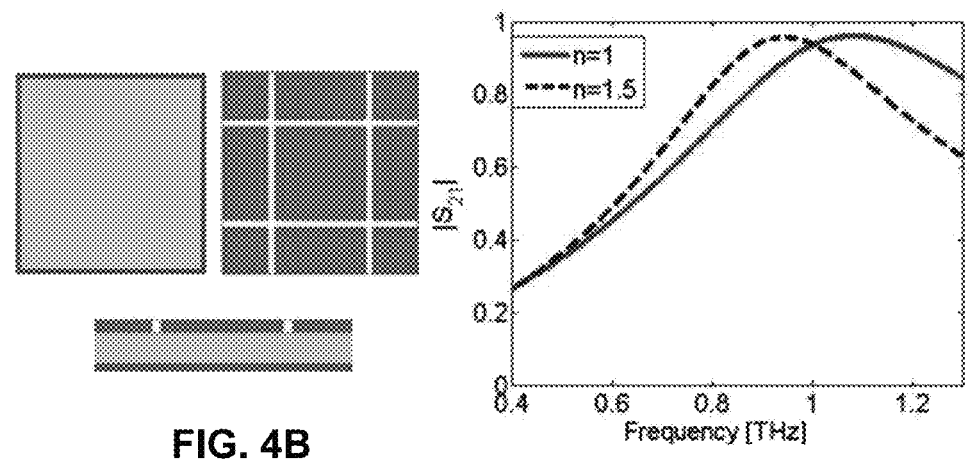
Figure 4C:
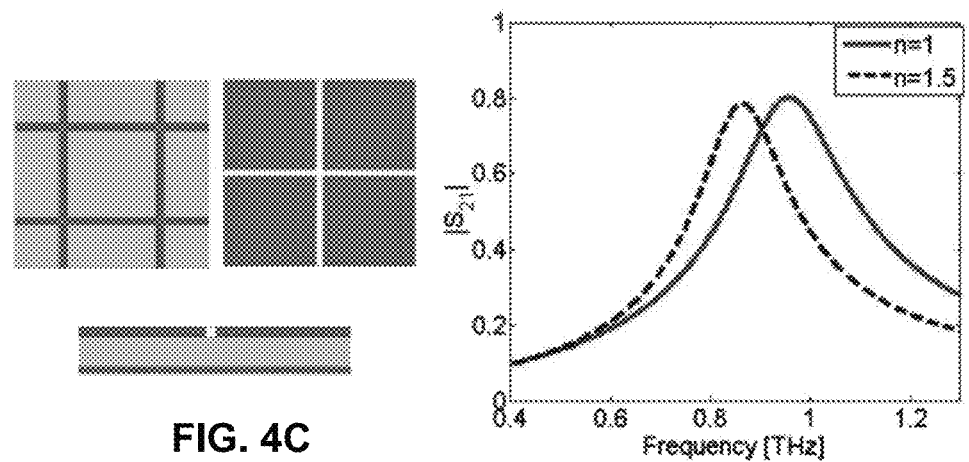

When the dielectric layer 25 between patch layer 23 and wire layer 24 is electrically thin ($\theta<\pi/6$, where $\theta$ is the electrical length of the dielectric layer) yet not too thin such that the patch and wire couple to each other directly, the short transmission line can be replaced by a Å network as shown in FIG. 3B. Furthermore for thin dielectric layer 25, the shunt capacitors $C_d$ are so small compared to $C_p$ and $L_w$ that they can be neglected. By doing this, circuit in FIG. 3C is obtained. Obviously, a transmission maxima will occur when $C_p$ is parallel resonant with $L_d$ and $L_w$. Peak value of the pass-band is determined by the ratio of $L_w$ and $L_d$. A narrow pass-band can be obtained by employing small inductance and large capacitance. This can be easily justified through full-wave simulation results in FIGS. 4A-4C. Small period of patch/wire means a small capacitance/inductance according to (1) and (2). As predicted before, a small inductance and a large capacitance configuration shown in FIG. 4C provides the narrowest pass-band. This merit is highly desired in bio-sensing because a narrow pass-band can make the change in n more distinguishable. Besides, the lower transmission in FIG. 4C is caused by the fact that smaller $L_w$ can only draw less portion of power from the inductor divider. Simulation results are summarized in Table I for comparison.

TABLE I

RESULTS SUMMARY OF PATCH-WIRE STRUCTURES

| | Resonant Frequency (THz) | Relative Resonant Frequency Shift $\left(\frac{f_{n1} - f_{n2}}{f_{n1}}\right)$ | Relative 3-dB Bandwidth $\left(\frac{f_H - f_L}{f_0}\right)$ | $|S_{21}|$ |
|---|---|---|---|---|
| FIG. 3 (a) | 0.705 | 11.3% | 34% | 0.941 |
| FIG. 3 (b) | 1.085 | 12.1% | 67.2% | 0.960 |
| FIG. 3 (c) | 0.955 | 10.6% | 22.5% | 0.800 |

Figure 5:
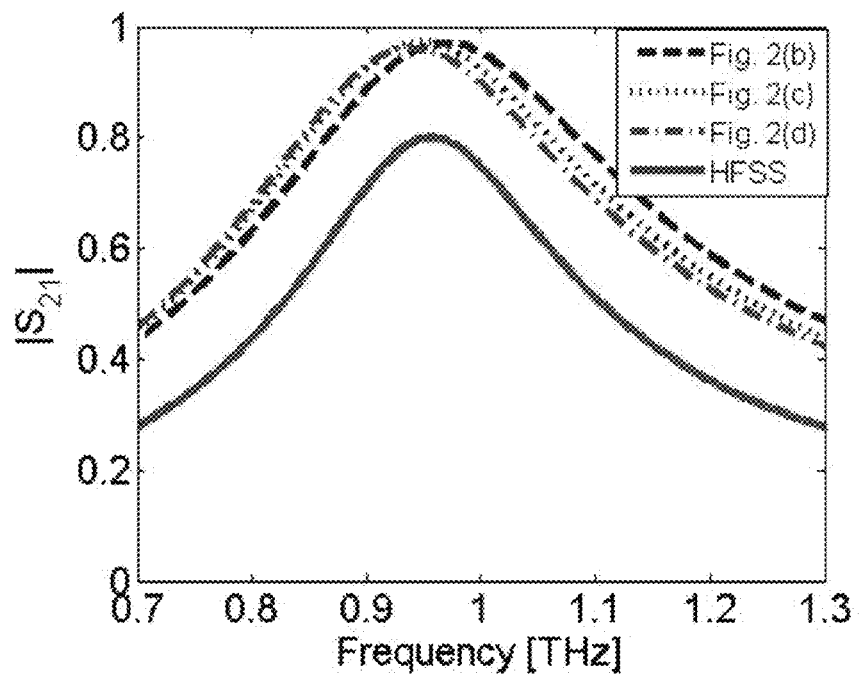
FIG. 5 is a graph depicting a comparison of simulation results between full-wave method and circuit models.

To validate proposed circuit model, a comparison between results obtained by full-wave simulation and circuit model simulation is shown in FIG. 5. Apparently, the circuit model can qualitatively predict the transmission curve, providing a physical insight into the operation scheme of this sensor. The discrepancy between the two curves is mainly caused by the omitted series reactance that is determined by the thickness of the reactance layer.

Figure 6A:
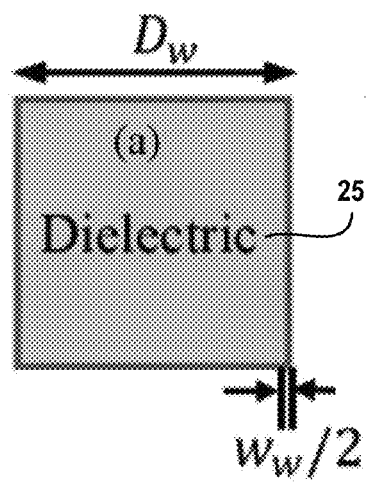
FIGS. 6A and 6B are top views of a dielectric coupling layer and an upper reactance layer for a second embodiment of a unit cell of the metamaterial sensor platform, respectively.
Figure 6B:
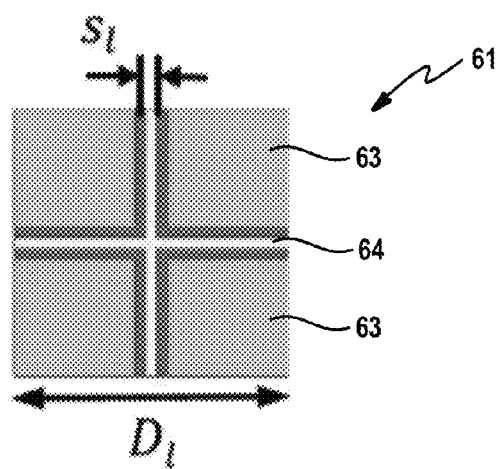
Figure 6C:
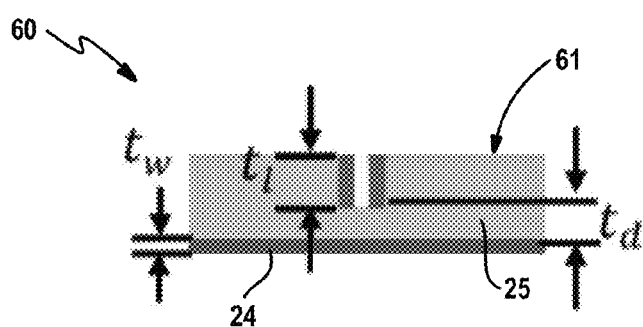
FIG. 6C is a cross-sectional view of the second embodiment of the unit cell of the metamaterial sensor platform.

In previous patch-wire structures, a huge capacitance is needed to narrow the pass-band. As can be seen from (1), one can either increase period of patch or decrease slot width to enhance capacitance. However, the period has to be controlled to be much smaller than the operating wavelength in order to stay in the metamaterial region; the slot width is also limited by the fabrication technology. One possible solution to this problem is to replace the patch layer with a loop layer 61 as shown in FIGS. 6A-6C.

In an example embodiment, a dielectric coupling layer 25 is sandwiched between a loop layer 61 and a wire layer 24. The loop layer 61 is comprised of an array of loop elements 63 embedded into the planar surface of the dielectric material forming the coupling layer 25, such that each loop element encircle a portion of the dielectric material. In the example embodiment, each of the loop elements 63 are in the shape of a square and the array is arranged as a grid. The loop elements 63 may take on other shapes, including triangles, hexagons, as well as other regular or irregular polygons. Likewise, the loop elements 63 may be arranged in other periodic or repeating patterns. Like the wire layer, the loop elements 63 are comprised of a metal, such as silver, gold or copper, or another type of conductive material. To host the sample material being interrogated, slots 64 are formed in between each of the loop elements 63. Each slot is sized to host a sample material.

Figure 7:
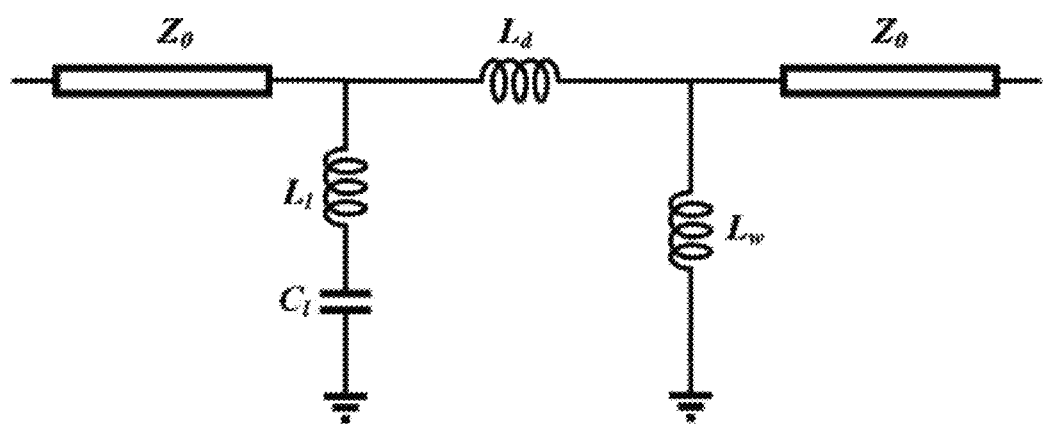
FIG. 7 is a circuit model for a unit cell of the second embodiment of the metamaterial sensor platform.
Figure 8A:
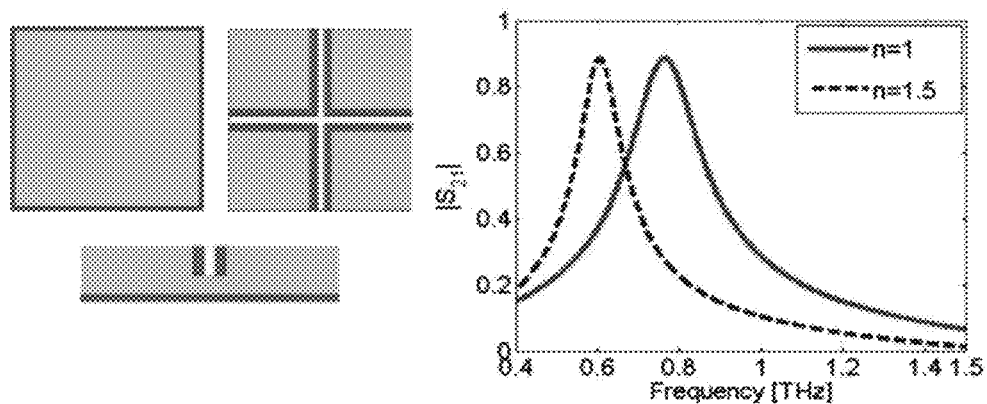
FIGS. 8A and 8B are graphs depicting full-wave simulation results for the second embodiment of the metamaterial sensor platform and a variant thereof.
Figure 8B:
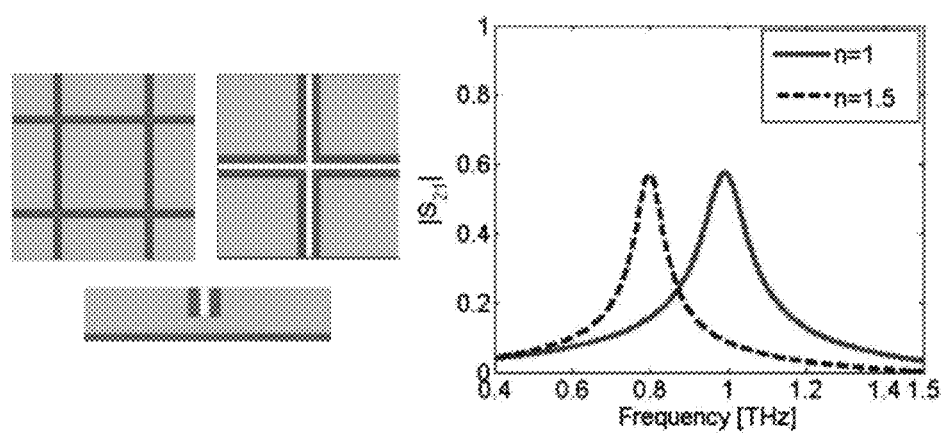

The loop layer 61 can be seen as a series branch composed of $C_l$ and $L_l$. These capacitor and inductor are associated with charge deposition between loop gap and current flowing along loop, respectively. The overall circuit model is shown in FIG. 7, where shunt capacitors brought by the transmission is again omitted. In the circuit model, a transmission zero is associated with the $L_l$-$C_l$ series breach. Close to this resonant point, this branch acts like a huge capacitance. This capacitance will parallel resonate with other reactance elements in the circuit to create a transmission maximum. This large huge and frequency-variant capacitance that can be exploited to sharpen the pass-band. Full-wave simulation results of this structure are shown in FIGS. 8A-8B. Similar to the patch-wire structure, smaller inductance $L_w$ corresponds to a narrower pass-band. The lower transmission peak is caused by the same reason as in the patch-wire structure: a smaller $L_w$ can only draw less power from the inductor divider. Table II lists simulation results for loop-wire structures.

TABLE II

RESULTS SUMMARY OF LOOP-WIRE STRUCTURES

| | Resonant Frequency (THz) | Relative Resonant Frequency Shift $\left(\frac{f_{n1} - f_{n2}}{f_{n1}}\right)$ | Relative 3-dB Bandwidth $\left(\frac{f_H - f_L}{f_0}\right)$ | $|S_{21}|$ |
|---|---|---|---|---|
| FIG. 6 (a) | 0.765 | 17.6% | 35.9% | 0.886 |
| FIG. 6 (b) | 0.99 | 19.6% | 16.6% | 0.576 |

One common yet minor drawback in patch-wire and loop-wire structures is that at the output stage, there is always an inductor divider to prevent all power being transferred. In order to sharpen the pass-band, a smaller $L_w$ is needed. This will, however, decrease output power. It seems feasible to decrease coupling inductance $L_d$ associated with the dielectric layer between two reactance layers to solve this problem. This, however, has two problems. One is that thickness of dielectric layer is limited by the fabrication process. Moreover, when the dielectric is too thin, direct electromagnetic coupling may occur between these two reactance layers, which is not expected in our case.

Figure 9A:
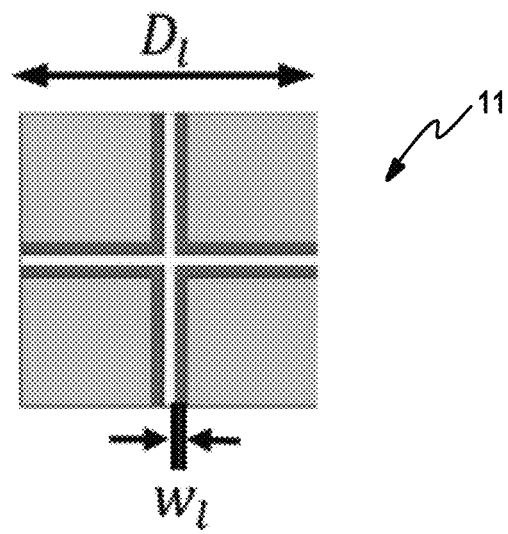
FIGS. 9A and 9B are a top view of an upper reactance layer and a bottom view of a lower reactance layer for a third embodiment of a unit cell of the metamaterial sensor platform, respectively.
Figure 9B:
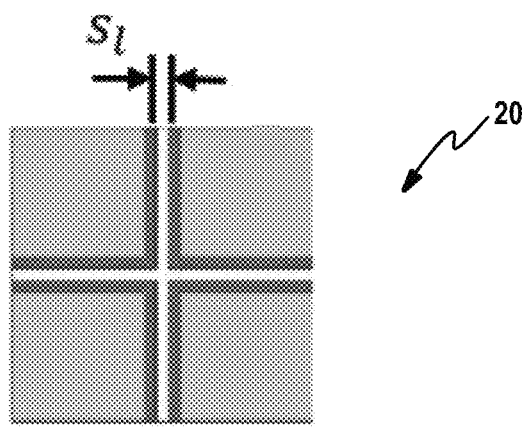
Figure 9C:
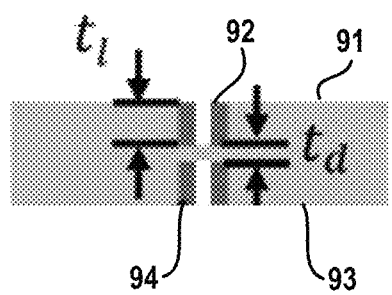
FIG. 9C is a cross-sectional view of the third embodiment of the unit cell of the metamaterial sensor platform.

One solution to this problem is a symmetrical loop structure shown in FIGS. 9A-9C. The upper reactance layer 11 and the lower reactance layer 13 are again separated by a coupling layer 12. In this embodiment, an array of loop elements is formed in each of the reactance layers 11, 12. That is, the coupling layer 12 is comprised of a dielectric material having opposing first and second planar surfaces 91, 93. A first array of loop elements 92 is formed in the first planar surface; whereas, a second array of loop elements 94 is formed in the second planar surface. The first array of loop elements 92 is formed symmetrically with the second array of loop elements 94. As noted above, the loop elements are dimensioned smaller than the operating wavelength. For loop elements in shape of a regular polygon, the length of each side of the polygon is smaller than the operating wavelength. Except with respect to this difference, the structure is substantially the same as described above in relation FIGS. 6A-6C.

Figure 10A:
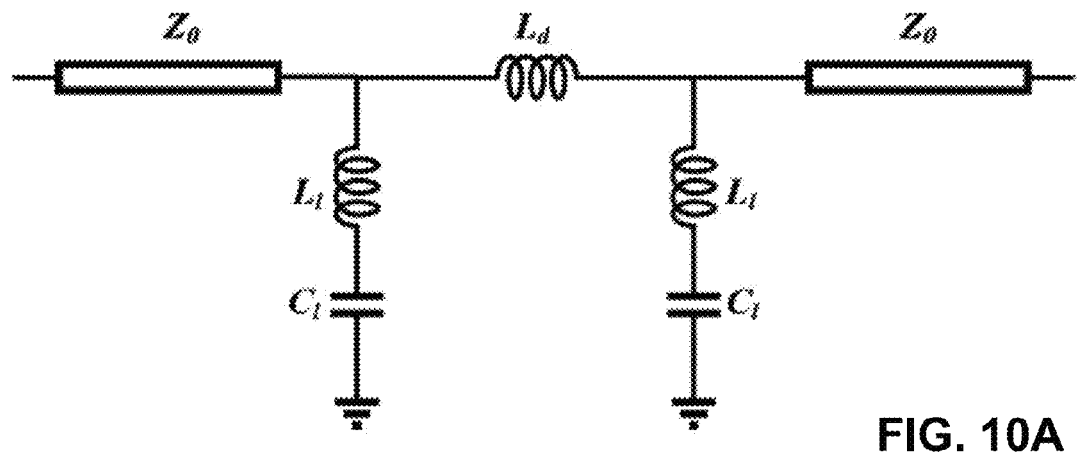
FIG. 10A is a circuit model for a unit cell of the third embodiment of the metamaterial sensor platform.
Figure 10B:
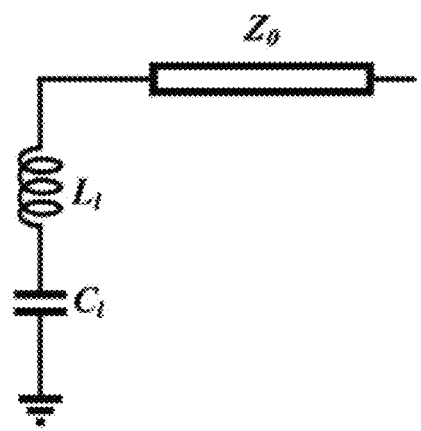
FIGS. 10B and 10C are an even mode circuit and an odd mode circuit, respectively, of the circuit model in FIG. 10A.
Figure 10C:
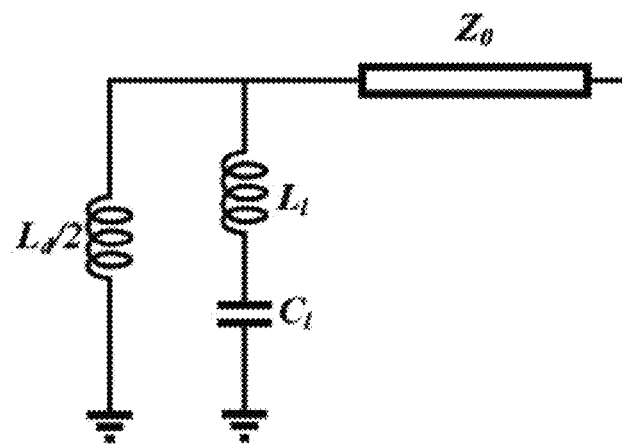

FIG. 10A depicts the circuit model of the embodiment shown in FIGS. 9A-9C. One obvious observation is that there is a transmission zero provided by the resonance of loop. Due to symmetry of this structure, an even-odd mode analysis is used to split the circuit into even and odd mode as shown in FIGS. 10B and 10C. Transmission coefficient of this circuit can be obtained in (3) through basic circuit theory.

$$S_1 = \frac{1}{2}\Gamma_e - \frac{1}{2}\Gamma_o \quad (3)$$

where $$\Gamma_e = \frac{z_e - z_0}{z_e + z_0}, \Gamma_o = \frac{z_o - z_0}{z_o + z_0},$$

$$Z_e = j\omega L_l - \frac{j}{\omega C_l}, Z_o = \frac{1}{\frac{1}{j\omega L_d/2} + \frac{1}{Z_e}}$$

Figure 11A:
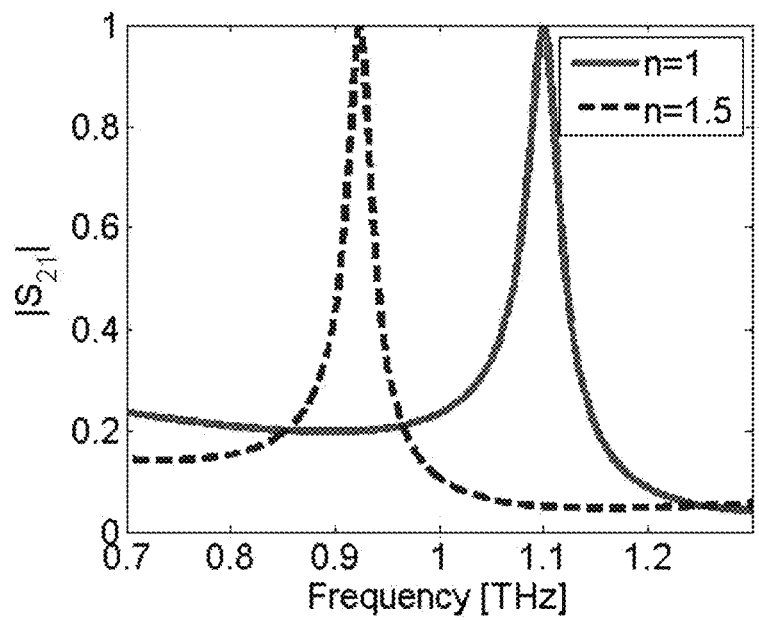
FIGS. 11A and 11B are graphs depicting full-wave simulation results for the third embodiment of the metamaterial sensor platform.

In (3), $S_{21}$ is the transmission coefficient from input to output; $\Gamma_e(\Gamma_o), Z_e(Z_o)$ are the reflection coefficient and the input impedance at output port for the even (odd) mode circuit, respectively. If the parallel resonance frequency of odd mode circuit $f_o$ is not far away from even mode circuit resonance frequency $f_e$, then $\Gamma_o$ is 1 and $\Gamma_e$ is around −1 at $f_o$ since $Z_e$, in this case, is much smaller than $Z_o$. Consequently, a transmission peak with a 100% power being transmitted can be achieved. Even when $f_o$ and $f_e$ are separated, there will always be a frequency below $f_o$ at which $Z_e$ is capacitive and $Z_o$ is inductive such that $\Gamma_o$ is equal to $-\Gamma_e$. Subsequently, $S_{21}$ is 1. Full-wave simulation result for this structure is shown in FIG. 11A. With this structure, samples are needed to be filled within the gaps between loops on both sides. An appropriate support to the samples on the backside is assumed here.

Figure 11B:
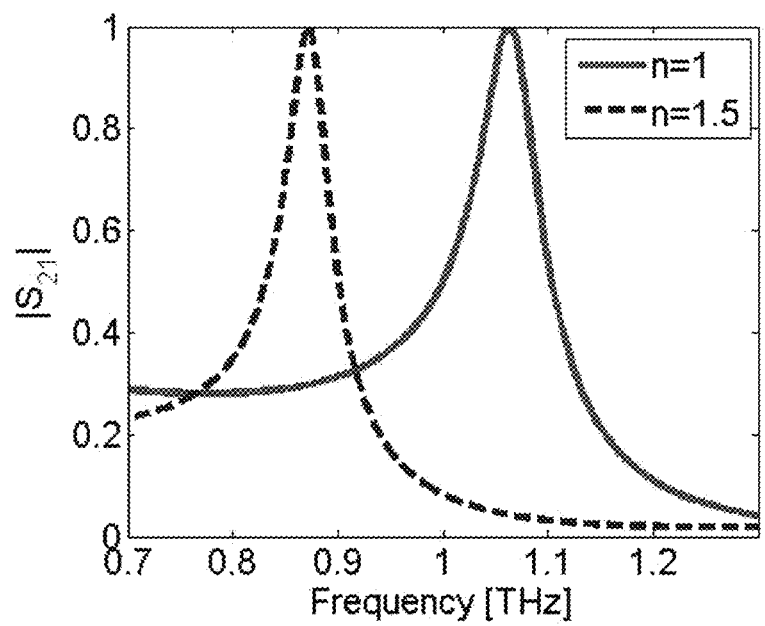

One interesting feature of this symmetrical loop structure is that the resonance frequency shift can be controlled by deliberate design. In this structure, the more $f_o$ is deviated from $f_e$, the further away $f_{ct}$ is located below $f_o$ since a smaller $Z_o$ is needed. Thus one can increase thickness of substrate to enhance $L_d$, which then provides a larger separation between $f_e$ and $f_o$ that can give rise to a larger frequency shift. Of course, a larger $L_d$ will, according to the circuit model, widen the pass-band. Therefore, a tradeoff can be made between narrow bandwidth and large resonance frequency shift. To illustrate this, simulation results of increasing $L_d$ is shown in FIG. 11B. The dimensions are also being modified to make it resonate at the same frequency. Simulation results are summarized in Table III for the purpose of comparison.

TABLE III

RESULTS SUMMARY OF SYMMETRICAL LOOP STRUCTURE

| | Resonant Frequency (THz) | Relative Resonant Frequency Shift $\left(\dfrac{f_{n1} - f_{n2}}{f_{n1}}\right)$ | Relative 3-dB Bandwidth $\left(\dfrac{f_H - f_L}{f_0}\right)$ | $|S_{21}|$ |
|---|---|---|---|---|
| FIG. 8 (a) | 1.102 | 16.0% | 2.5% | 0.986 |
| FIG. 8 (b) | 1.062 | 17.8% | 3.3% | 0.999 |

Figure 12:
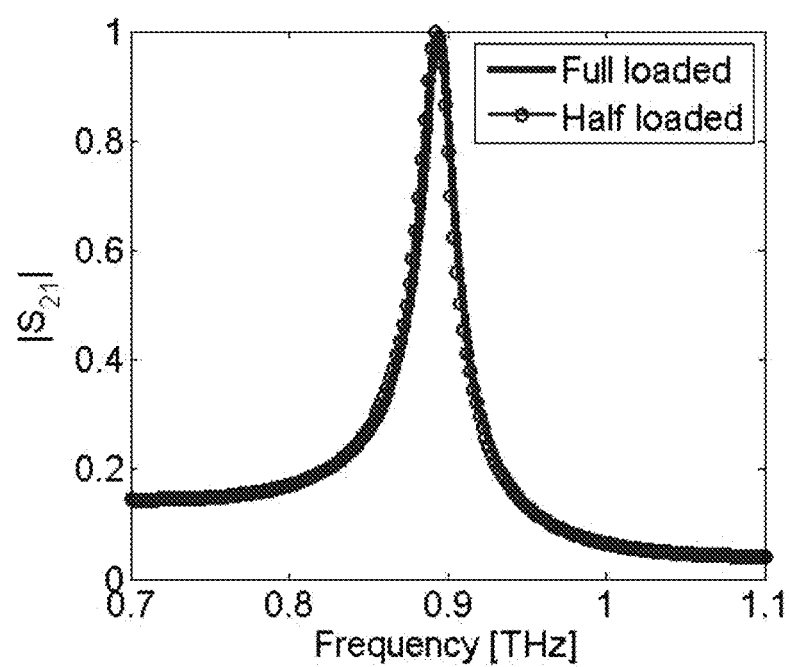
FIG. 12 is a graph depicting a comparison of results obtained from a sensor with all slots loaded with sample and sensor with only half slots are loaded.

In addition, the amount of sample needed in a test can be reduced by half if one uses an appropriate polarization of incident wave. Only slots perpendicular to the electric field needs to be filled since electric field mainly interacts with these slots. FIG. 12 plots the transmission curves obtained from sensor with all the slots filled and sensor with only slots perpendicular to the electric field polarization direction filled. Apparently, there is no practical difference between these two curves. Therefore, amount of sample needed is reduced.

Figure 13:
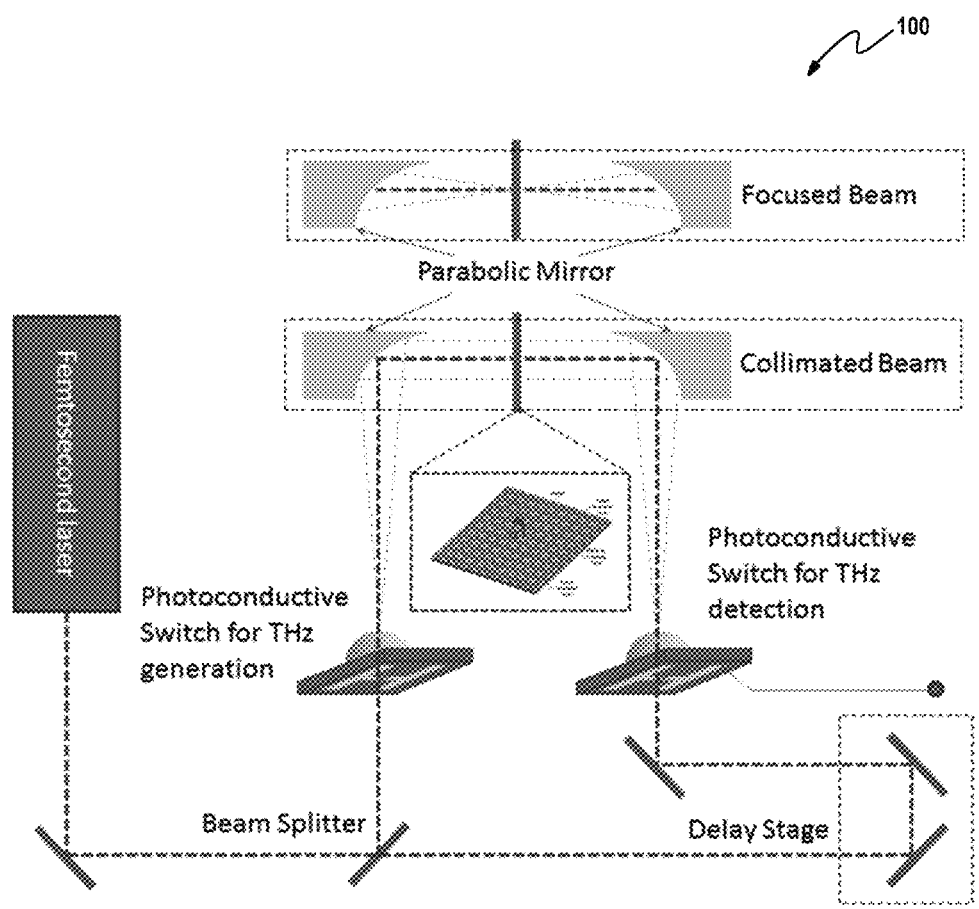
FIG. 13 is a diagram on an example bio-sensor using the metamaterial platform.

FIG. 13 depicts an example bio-sensor 100 which includes the metamaterial platform 10. The bio-sensor 100 employs a free-space design. Compared with the waveguide-based sensing structure, the metamaterial platform 10 is straight-forward for integration with the THz-TDS measurement systems. In FIG. 1, platform 10 is placed on the path of the THz probing signals. The probing signal can be either collimated or focused, depending on the scale of the sensing functionalities. In parallel sensing, parabolic mirrors are used to collimate the signal, which will impinge on an array of sensors simultaneously. In point sensing, the THz pulses are focused, and hemispherical lenses may be used for further shrinking the spot size. The bio-samples can be applied to the surface of the platform 10 more easily as it is an open structure and can be in the form of powder, gel, thin film, or solutions. Controlled humidity can also be applied to obtain and maintain the desired hydration level.

In summary, different metamaterial platform have been proposed for use in DNA sensors. Design guideline based on circuit model counterparts is outlined in this disclosure. Full-wave simulation results validate the high sensitivity achieved by proposed sensors.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A sensor platform for interrogating a sample with an electromagnetic (EM) wave having a given operating wavelength, comprising:
   a dielectric material having opposing first and second planar surfaces;
   a first array of loop elements embedded in the first planar surface of the dielectric material, wherein slots are formed between each of the loop elements in the first array of loop elements and are configured to host a sample material therein; and
   a second array of loop elements embedded in the second planar surface of the dielectric material and formed symmetrically with respect to the first array of loop elements, wherein slots are formed between each of the loop elements of the second array of loop elements and the loop elements in the first array and the second array are comprised of a conductive material.

2. The sensor platform of claim 1 wherein the loop elements in the first array and the second array are dimensioned smaller than the given operating wavelength.

3. The sensor platform of claim 1 wherein the loop elements in the first array and the second array are dimensioned for an electromagnetic (EM) wave having a frequency on the order of one terahertz.

4. The sensor platform of claim 1 wherein the loop elements in the first array and the second array have a shape selected from a group consisting of a square, a triangle and a hexagon.

5. The sensor platform of claim 1 wherein the loop elements in the first array and the second array are in a grid arrangement.

6. The sensor platform of claim 1 wherein each loop element in the first array of loop elements encircles a portion of the dielectric material and each loop element in the second array of loop elements encircles a portion of the dielectric material.

7. The sensor platform of claim 1 wherein the dielectric material is one of SU-8 or Parylene.

8. The sensor platform of claim 1 wherein the conductive material is one of silver, gold or copper.

9. A sensor platform for interrogating a sample with an electromagnetic (EM) wave having a given operating wavelength, comprising:
   a dielectric material having opposing first and second planar surfaces;
   a first array of loop elements embedded in the first planar surface of the dielectric material upon which the electromagnetic wave is incident, slots are formed between the loop elements in the first array of loop elements and are sized to host a sample material therein; and a second array of loop elements embedded in the second planar surface of the dielectric material and formed symmetrically with respect to the first array of loop elements, slots are formed between the loop elements of the second array of loop elements and are sized to host a sample material therein, wherein the loop elements in the first array and the second array are in shape of a regular polygon having dimensions smaller than the given operating wavelength.

10. The sensor platform of claim 9 wherein the loop elements in the first array and the second array are dimensioned for an electromagnetic (EM) wave having a frequency on the order of one terahertz.

11. The sensor platform of claim 9 wherein the loop elements in the first array and the second array have a shape selected from a group consisting of a square, a triangle and a hexagon.

12. The sensor platform of claim 9 wherein the loop elements in the first array and the second array are in a grid arrangement.

13. The sensor platform of claim 9 wherein each loop element in the first array of loop elements encircles a portion of the dielectric material and each loop element in the second array of loop elements encircles a portion of the dielectric material.

14. The sensor platform of claim 9 wherein the dielectric material is one of SU-8 or Parylene.

15. The sensor platform of claim 9 wherein the loop elements in the first and second array are comprised of a metal.

* * * * *